US007633502B2

(12) United States Patent
Willis et al.

(10) Patent No.: US 7,633,502 B2
(45) Date of Patent: Dec. 15, 2009

(54) SYSTEM AND METHOD FOR GRAPHICALLY REPRESENTING ANATOMICAL ORIFICES AND VESSELS

(75) Inventors: N. Parker Willis, Atherton, CA (US); Ren-Her Hwang, Milpitas, CA (US); Jinglin Zeng, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1514 days.

(21) Appl. No.: 10/850,357

(22) Filed: May 19, 2004

(65) Prior Publication Data

US 2005/0261580 A1 Nov. 24, 2005

(51) Int. Cl.
G06T 17/00 (2006.01)

(52) U.S. Cl. .................. 345/420; 600/462; 345/441
(58) Field of Classification Search .............. 345/420, 345/441, 633, 636; 600/459, 462, 463
See application file for complete search history.

(56) References Cited

U.S. PATENT DOCUMENTS

| | | | |
|---|---|---|---|
| 5,383,874 | A | 1/1995 | Jackson et al. |
| 5,391,199 | A | 2/1995 | Ben-Haim |
| 5,485,849 | A | 1/1996 | Panescu et al. |
| 5,494,042 | A | 2/1996 | Panescu et al. |
| 5,724,978 | A | 3/1998 | Tenhoff |
| 5,818,424 | A * | 10/1998 | Korth .................. 345/158 |

(Continued)

FOREIGN PATENT DOCUMENTS

EP 1 125 549 A2 8/2001

(Continued)

OTHER PUBLICATIONS

PCT International Search Report for PCT/US2005/017422, Applicant: Boston Scientific Scimed, Inc., Forms PCT/ISA/210 and 220, dated Sep. 15, 2005 (6 pages).

(Continued)

*Primary Examiner*—Kee M Tung
*Assistant Examiner*—Michelle K Lay
(74) *Attorney, Agent, or Firm*—Vista IP Law Group LLP

(57) ABSTRACT

Methods and systems are provided for generating graphical representations of orifices and vessels. One method comprises generating a representation of the surface (e.g., an endocardial surface) within a coordinate system, and laterally moving the distal end of an elongated probe within an orifice (e.g., a valve or a vessel ostium) associated with the surface. The method further comprises defining line segments within the coordinate system while the probe distal end is moved within the orifice, wherein each of the line segments represents the probe distal end. The method further comprises defining intersection points within the coordinate system, wherein each of the points represents an intersection of one of the line segments and the surface representation. Lastly, the method comprises graphically generating a representation of the orifice based on the intersection points, e.g., by forming the orifice representation around the intersection points. Another method comprises moving the distal end of an elongated probe within the vessel, defining line segments within a coordinate system while the probe distal end is moved within the vessel, wherein each of the line segments represents the probe distal end, and graphically generating a representation of the vessel based on the line segments.

26 Claims, 11 Drawing Sheets

U.S. PATENT DOCUMENTS

| | | | |
|---|---|---|---|
| 5,830,145 A * | 11/1998 | Tenhoff | 600/463 |
| 5,833,621 A | 11/1998 | Panescu et al. | |
| 5,898,793 A | 4/1999 | Karron et al. | |
| 5,983,126 A | 11/1999 | Wittkampf | |
| 6,019,725 A | 2/2000 | Vesely et al. | |
| 6,101,409 A | 8/2000 | Swanson et al. | |
| 6,102,861 A | 8/2000 | Avila et al. | |
| 6,216,027 B1 | 4/2001 | Willis et al. | |
| 6,226,542 B1 | 5/2001 | Reisfeld | |
| 6,295,464 B1 | 9/2001 | Metaxas | |
| 6,301,496 B1 * | 10/2001 | Reisfeld | 600/407 |
| 6,342,889 B1 | 1/2002 | Callahan | |
| 6,381,026 B1 | 4/2002 | Shiff et al. | |
| 6,389,310 B1 | 5/2002 | Demonceau et al. | |
| 6,490,474 B1 | 12/2002 | Willis et al. | |
| 6,491,632 B1 | 12/2002 | Taylor | |
| 6,606,089 B1 | 8/2003 | Margadant | |
| 6,650,927 B1 | 11/2003 | Keidar | |
| 6,692,430 B2 | 2/2004 | Adler | |
| 6,711,429 B1 | 3/2004 | Gilboa et al. | |
| 2003/0191463 A1 | 10/2003 | Stewart et al. | |
| 2004/0030249 A1 | 2/2004 | Willis | |

FOREIGN PATENT DOCUMENTS

| | | |
|---|---|---|
| WO | WO 98/29032 | 7/1998 |
| WO | WO 00/07501 | 2/2000 |

OTHER PUBLICATIONS

PCT Written Opinion of the International Search Authority for PCT/US2005/017422, Applicant: Boston Scientific Scimed, Inc., Form PCT/ISA/237, dated Sep. 15, 2005 (6 pages).

* cited by examiner

SYSTEM AND METHOD FOR GRAPHICALLY REPRESENTING ANATOMICAL ORIFICES AND VESSELS

FIELD OF THE INVENTION

The present inventions generally relate to medical probes, and more particularly to systems and methods for navigating medical probes within anatomical organs or other anatomical structures.

BACKGROUND OF THE INVENTION

It is often necessary or desirable to determine the location of a medical probe relative to a location of interest within three-dimensional space. In many procedures, such as interventional cardiac electrophysiology therapy, it is important for the physician to know the location of a probe, such as a catheter, (especially, a therapeutic catheter) relative to the patient's internal anatomy. During these procedures, a physician, e.g., steers an electrophysiology mapping catheter through a main vein or artery into the interior region of the heart that is to be treated. The physician then determines the source of the cardiac rhythm disturbance (i.e., the targeted cardiac tissue) by placing mapping elements carried by the catheter into contact with the heart tissue, and operating the mapping catheter to generate an electrophysiology map of the interior region of the heart. Having identified the targeted cardiac tissue, the physician then steers an ablation catheter (which may or may not be the same catheter as the mapping catheter above) into the heart and places an ablating element carried by the catheter tip near the targeted cardiac tissue, and directs energy from the ablating element to ablate the tissue and form a lesion, thereby treating the cardiac disturbance.

In certain advanced electrophysiology procedures, it is desirable to create a lesions around, within, or otherwise adjacent to orifices. For example, as part of the treatment for certain categories of atrial fibrillation, it may be desirable to create a curvilinear lesion around or within the ostia of the pulmonary veins (PVs), and a linear lesion connecting one or more of the PVs to the mitral valve annulus. To do this, a physician must be able to move the ablation catheter tip along a desired path and either deliver ablative energy while slowly dragging the tip along the path, or deliver energy at a number of discrete points along that path. Either way, it is crucial that the physician be able to accurately and controllably move the catheter tip along that path by referencing anatomical structures, such as the ostium of the PV's and the mitral valve annulus. More importantly, during the electrophysiology procedure, it is important to prevent inadvertent damage to non-targeted regions, such as the PVs themselves, which could produce stenosis of the PVs.

Traditionally, navigation of catheters relative to points of interest has been accomplished using fluoroscopy. In this case, radiopaque elements are located on the distal end of the catheter and fluoroscopically imaged as the catheter is routed through the body. As a result, a two-dimensional image of the catheter, as represented by the illuminated radiopaque elements, is generated, thereby allowing the physician to roughly determine the location of the catheter. The use of fluoroscopy in locating catheters is somewhat limited, however, in that the physician is only able to visualize the catheter and surrounding tissues in two dimensions. In addition, fluoroscopy does not image soft tissues, making it difficult for the physician to visualize features of the anatomy as a reference for the navigation. Thus, fluoroscopy is sub-optimal for the purpose of navigating a catheter relative to anatomical structure composed primarily of soft tissues, e.g., within the heart.

Various types of three-dimensional medical systems (e.g., the Realtime Position Management™ (RPM) tracking system, developed commercially by Boston Scientific Corporation and described in U.S. Pat. No. 6,216,027 and U.S. patent application Ser. No. 09/128,304, entitled "A Dynamically Alterable Three-Dimensional Graphical Model of a Body Region," and the CARTO EP Medical system, developed commercially by Biosense Webster and described in U.S. Pat. No. 5,391,199) have been developed, or at least conceived, to address this issue. In these medical systems, a graphical representation of the catheter or a portion thereof is displayed in a three-dimensional computer-generated representation of a body tissue, e.g., a heart chamber. The three-dimensional representation of the body tissue is produced by mapping the geometry of the inner surface of the body tissue in a three-dimensional coordinate system, e.g., by moving a mapping device to multiple points on the body tissue. The position of the device to be guided within the body tissue is determined by placing one or more location elements on the device and tracking the position of these elements within the three-dimensional coordinate system.

These medical systems can also be used to define orifices and vessels by placing the mapping device adjacent to these anatomical locations. In particular, a user may define an orifice, which may represent an ostium of a vessel or a valve opening, by placing the tip of the mapping device at multiple locations on the annular surface around the orifice. However, this can be a tedious and time consuming process, since the tip of the mapping device must be carefully placed on the annular surface that defines the orifice. For example, if the tip of the mapping device is actually placed within the orifice or on a portion of the endocardial surface too far away from the orifice, the resulting graphical image of the orifice will be inaccurate and not very well-defined. A user may also define a vessel by placing the tip of the mapping device through the ostium of the vessel and touching the endothelial surface at various points along the vessel. However, because many points are required to provide an accurate graphical representation of the vessel, and because the tip of a mapping device is not well suited for defining the wall of an elongated anatomical structure, graphical vessel construction using current technologies can also be a tedious and time-consuming process.

There thus remains a need for an improved system and method for graphically defining and representing anatomical orifices and vessels.

SUMMARY OF THE INVENTION

In accordance with a first aspect of the present inventions, a method of graphically creating a representation of an anatomical body having a surface with an orifice is provided. The anatomical body can be, e.g., a heart chamber, and the orifice can be, e.g., an ostium of a blood vessel, such one of the pulmonary vein ostia, or a valve, such as the mitral valve. The method comprises graphically generating a representation of the surface within a coordinate system, and preferably a three-dimensional coordinate system.

The method further comprises laterally moving the distal end of an elongated probe within the orifice, and defining line segments (representing the probe distal end) within the coordinate system while the probe distal end is moved within the orifice. In one method, the line segments are rectilinear (i.e., straight), although the line segments may be curvilinear. In one method, each line segment is defined by determining at least two points along the probe distal end within the coordinate system.

The method further comprises defining intersection points within the coordinate system, each of the points representing an intersection of one of the line segments and the surface representation, and graphically generating a representation of the orifice based on the intersection points. In one method, the step of graphically generating the orifice representation comprises connecting outermost intersection points with lines to form a polygon. In another method, the step of graphically generating the orifice representation comprises fitting an ellipse around the intersection points.

Optionally, the method comprises graphically regenerating a representation of the surface, redefining new intersection points within the coordinate system, each of the new points representing an intersection of one of the line segments and the regenerated graphical surface representation, and graphically regenerating a representation of the orifice based on the new intersection points. If the anatomical body has a vessel, in which case, the orifice may be an ostium of the vessel, the method may optionally comprise graphically generating a representation of the vessel based on the line segments. For example, the step of graphically generating the vessel representation may comprise forming the graphical vessel representation around the line segments.

In accordance with another aspect of the present inventions, a medical system for use within the previously described anatomical body is provided. The medical system comprises an elongated medical probe (such as an intravascular catheter) having a distal section with a known geometry, e.g., a straight probe section. The medical system further comprises one or more processors configured for performing the previously described line segment definition and graphical surface and orifice representation generation steps, and an optional output device for displaying the surface and orifice representations.

In accordance with the present inventions, a method of graphically creating a representation of an elongated anatomical vessel, such as a blood vessel (e.g., a pulmonary vein), is provided. The method comprises moving the distal end of an elongated probe within the vessel and defining line segments (representing the probe distal end) within the coordinate system while the probe distal end is moved within the vessel. In one method, the line segments are rectilinear (i.e., straight), although the line segments may be curvilinear. In one method, each line segment is defined by determining at least two points along the probe distal end within the coordinate system. If the vessel has an ostium, the method may optionally comprise graphically generating a representation of the ostium, which may be based on the line segments.

In accordance with one aspect of the present inventions, the method further comprises graphically generating a representation of the vessel based on the line segments. For example, in one method, the step of graphically generating the vessel representation comprises forming the vessel representation around the line segments.

In accordance with another aspect of the present invention, the method comprises defining an initial disk based on a central region of the line segment grouping. In one method, the step of defining the initial disk comprises defining a bounding box around the line segments, and locating an initial line segment that is closest to a center point of the bounding box, wherein the initial disk is oriented along the initial line segment. The method further comprises defining one or more proximal subsequent disks based on one or more respective proximal regions of the line segment grouping, and defining one or more distal subsequent disks based on one or more respective distal regions of the line segment grouping. In one method, the central, proximal, and distal regions of the line segment grouping overlap. The method may further comprise graphically generating a representation of the vessel around the initial and subsequent disks.

In another method, the definition of each of the proximal disks is based at least partially on the definition of the closest distally neighboring disk, and the definition of each of the distal disks is based at least partially on the definition of the closest proximally neighboring distal disk. For example, the orientation of the proximal and distal disks neighboring the initial disk can have the same orientation as the initial disk, the orientation of each of the remaining proximal disks can have an orientation defined by a vector formed by center positions of the two closest distally neighboring disks, and the orientation of each of the remaining distal disks can have an orientation defined by a vector formed by center positions of the two closest proximally neighboring disks. Also, each proximal disk may be separated by a predetermined distance from a center point of the closest distally neighboring disk along an orientation vector of the respective proximal disk, and each distal disk may be separated by a predetermined distance from a center point of the closest proximally neighboring disk along an orientation vector of the respective distal disk.

In another method, each disk has a center position that is defined by projecting at least one point of a plurality of line segments onto a plane, and defining a bounding box around the projected points, wherein the center of the bounding box defines the center position of the respective disk. The radius of the disk may be defined by the distance between the center of the bounding box and the farthest projected point. The projected points may be determined in any one of a variety of manners, but in one method, two parallel planes are equidistantly separated from an initial plane until a predetermined number of points (comprising end points of line segments and intersection points between the line segments and the two planes) reside between the two planes. In this case, the points between the planes will be the projected points and the initial plane will be the projected plane.

Optionally, the disks can be subsequently redefined to provide a more accurate representation of the vessel. For example, the method may further comprise reorienting each of the disks based on the orientations of the closest proximally and distally neighboring disks. In one method, the reorientation of each of the disks is based on the average of respective orientation vectors of the closest proximally and distally neighboring disks. The method may further comprise performing a smoothing function on the disks. For example, the smoothing function may comprise redefining each of the disks with a new radius based on the average of the radii of the respective disk and the closest proximally and distally neighboring disks, and redefining each of the disks with a new center point based on the average of the orientation vectors of the respective disk and the closest proximally and distally neighboring disks.

In accordance with another aspect of the present inventions, a medical system for use within the previously described anatomical body is provided. The medical system comprises an elongated medical probe (such as an intravascular catheter) having a distal section with a known geometry, e.g., a straight probe section. The medical system further comprises one or more processors configured for performing the previously described line segment definition and graphical vessel representation generation steps, and an optional output device for displaying the vessel representation.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
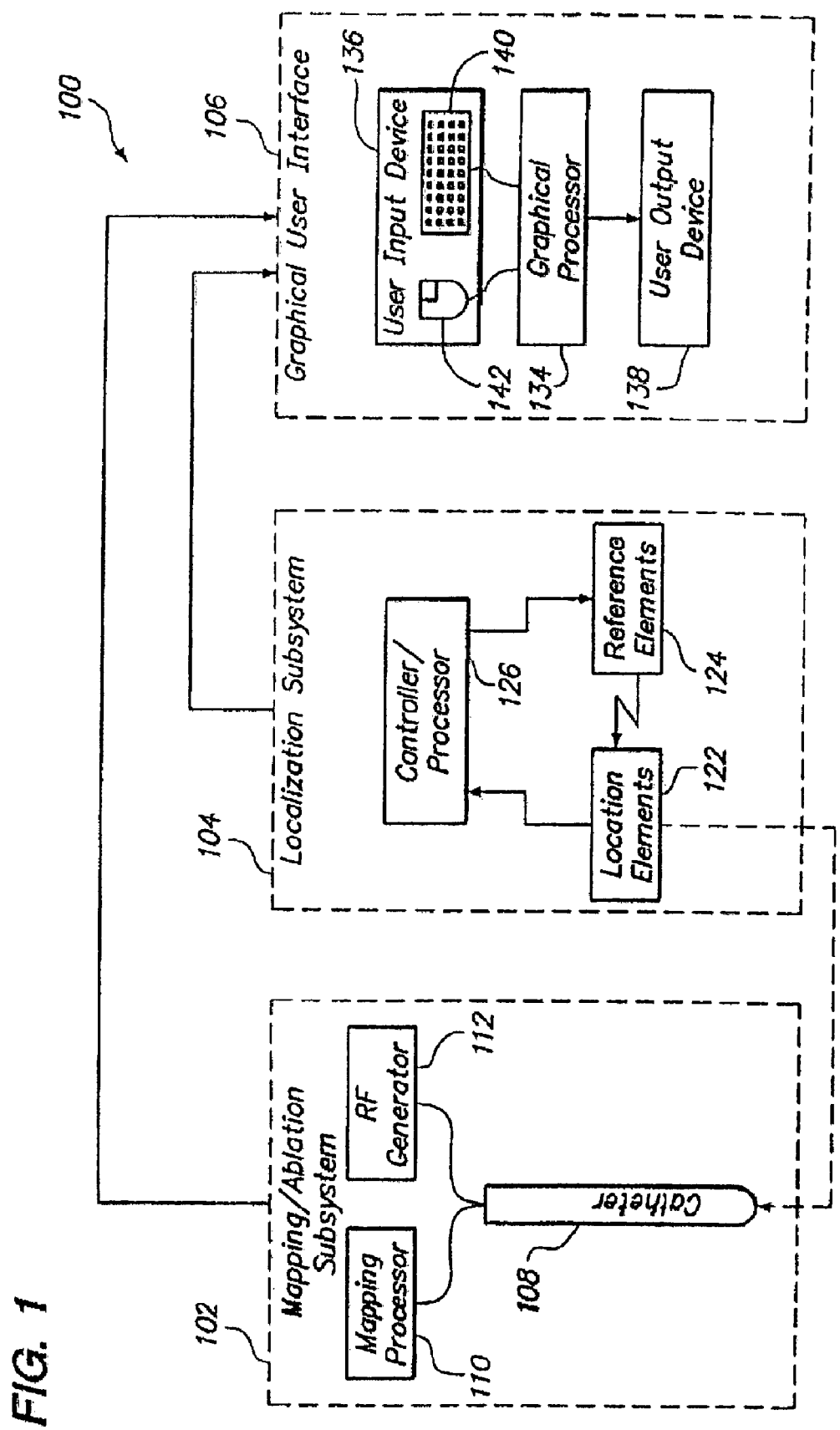
FIG. 1 is a functional block diagram of one preferred embodiment of a medical system constructed in accordance with the present inventions.
Figure 2:
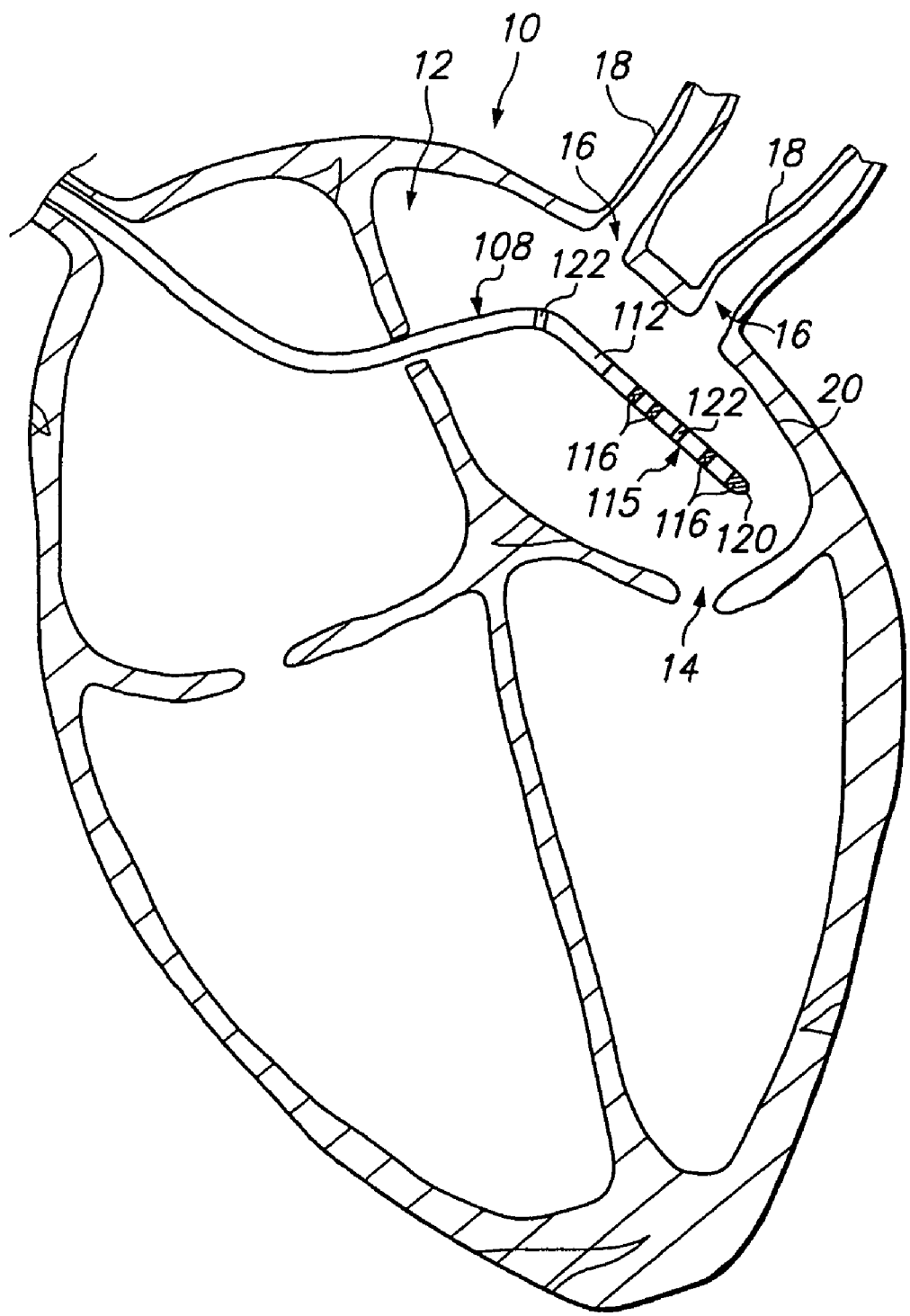
FIG. 2 is a view of a mapping/ablation catheter disposed within the left atrium of a heart.

Referring to FIG. 1, an exemplary medical system 100 constructed in accordance with the present invention is shown. The medical system 100 is particularly suited for mapping and treating a heart 10 (shown in FIG. 2) with catheters. Nevertheless, it should be appreciated that it can be used for treating, diagnosing, or otherwise graphically reconstructing other internal hollow anatomical structures with orifices, such as valves and blood vessel ostia, and can be used with medical devices other than catheters. In the specific method described herein, the medical system 100 will be used to graphically reconstruct the endocardial surface 20 of the left atrium 12, the mitral valve 14, and ostia 16 of the pulmonary veins 18, as illustrated in FIG. 2.

The medical system 100 generally comprises (1) a mapping/ablation subsystem 102 for mapping and ablating tissue within the heart 10; (2) a localization subsystem 104 for registering mapping data and the movement of a probe within a three-dimensional coordinate system; and (3) a graphical user interface 106 configured for generating and displaying graphics of the heart 10 and associated anatomical structures, mapping data, and probe within the three-dimensional coordinate system. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

I. Mapping/Ablation Subsystem

The mapping/ablation subsystem 102 is configured to identify and treat a target tissue site or sites, e.g., aberrant conductive pathways. To this end, the mapping/ablation subsystem 102 comprises a mapping/ablation catheter 108, a mapping processor 110, and a radio frequency (RF) generator 112. As further illustrated in FIG. 3, the mapping/ablation catheter 108 comprises an elongate catheter member 114, a plurality of electrodes 116 (in this case, four) carried at the distal end of the catheter member 114, and a handle 118 carried at the proximal end of the elongate member 114. All four electrodes 116 on the catheter member 114 are configured to detect electrical signals in the myocardial tissue for subsequent identification of target sites. The electrode 116 at the distal tip 120 of the catheter member 114 is also configured to be used as an ablation electrode to provide ablation energy to the targeted sites when placed adjacent thereto and operated. The handle 118 includes an electrical connector (not shown) for electrical coupling to the mapping processor 110 and RF generator 112.

The distal end of the catheter member 114 comprises a rigid or semi-rigid section 115 that assumes a preshaped and known geometry in the absence of an external force. In particular, the pre-shaped catheter section 115 of the catheter member 114, although somewhat flexible when being navigated through the vasculature leading to the heart 10, maintains the preshaped geometry when navigated within the chambers of the heart 10 and associated anatomical structures, such as the heart valves and vessel ostia. In the illustrated embodiment, the preshaped catheter section 115 is straight, although a curved geometry may be used, as long as it is well-defined.

Referring back to FIG. 1, the mapping processor 110 is configured to derive activation times and voltage distribution from the electrical signals obtained from the electrodes 116 to determine irregular electrical signals within the heart, which can then be graphically displayed as a map. Mapping of tissue within the heart 10 is well known in the art, and thus for purposes of brevity, the mapping processor 110 will not be described in further detail. Further details regarding electrophysiology mapping are provided in U.S. Pat. Nos. 5,485,849, 5,494,042, 5,833,621, and 6,101,409, which are expressly incorporated herein by reference.

The RF generator 112 is configured to deliver ablation energy to the ablation electrode (i.e., the distal most electrode 116) in a controlled manner in order to ablate sites identified by the mapping processor 110. Alternatively, other types of ablative sources besides the RF generator 112 can be used, e.g., a microwave generator, an acoustic generator, a cryoablation generator, and a laser or other optical generator. Ablation of tissue within the heart is well known in the art, and thus for purposes of brevity, the RF generator 112 will not be described in further detail. Further details regarding RF generators are provided in U.S. Pat. No. 5,383,874, which is expressly incorporated herein by reference.

It should be noted that other types of mapping/ablation catheters can be used in the medical system 100. For example, a catheter having a basket structure of resilient splines, each of which carries a plurality of dedicated mapping electrodes can be used. This catheter may be placed in a heart chamber, so that the resilient splines conform to the endocardial surface of the heart, thereby placing and distributing the mapping electrodes along the entire endocardial surface of the cavity for efficient mapping. The catheter may also have a roving ablation electrode that can be steered in contact with the ablation sites identified by the mapping electrodes. Or a separate ablation catheter with a dedicated ablation electrode or electrodes can be used.

II. Localization Subsystem

Figure 3:
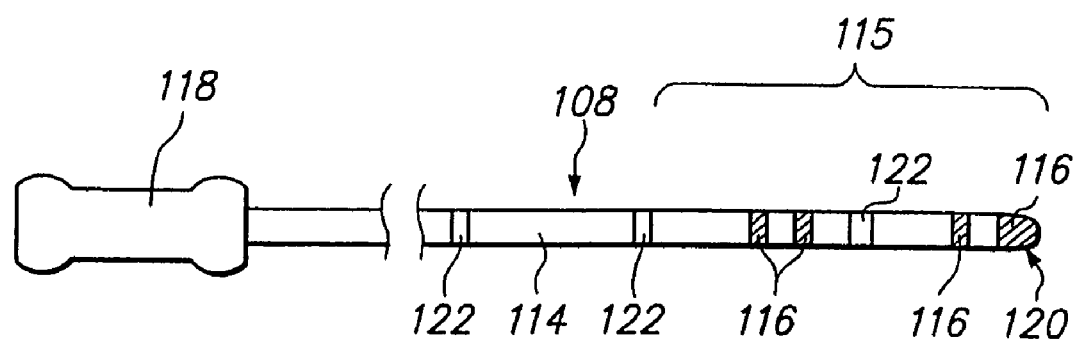
FIG. 3 is a plan view of a mapping/ablation catheter used in the medical system of FIG. 1.

Referring still to FIG. 1, the localization subsystem 104 includes a plurality of location elements 122, a plurality of reference elements 124, and a controller/processor 126 coupled to the reference elements 124 and location elements 122. As shown in FIG. 3, the location elements 122 (in this case, three) are carried by the distal end of the mapping/ablation catheter 108. Significantly, two of the location elements 122 are located on the straight catheter section 115. It should be noted that although the location elements 122 are carried by the mapping/ablation catheter 108, alternatively, the location elements 122 may be located on a separate device having a pre-shaped distal end, e.g., if the mapping/ablation catheter takes the form of a basket structure.

Figure 4:
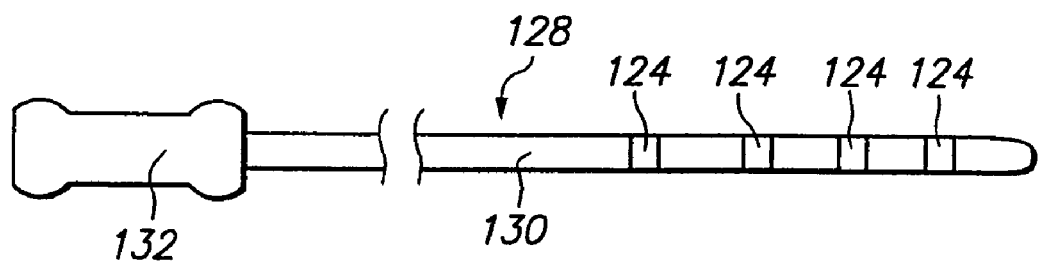
FIG. 4 is a plan view of a reference catheter used in the medical system of FIG. 1.

As shown in FIG. 4, at least some of the reference elements 124 are carried by a reference catheter 128. Like the mapping/ablation catheter, the reference catheter 128 comprises an elongate catheter member 130 and a handle 132 carried at the proximal end of the elongate member 130. The distal end of the reference catheter 128 may optionally comprise a plurality of electrodes (not shown), e.g., to provide the reference catheter 128 with mapping functionality. The reference catheter 128 may be affixed within selected regions of the heart 10, in order to establish an internal three-dimensional coordinate system, as will be further discussed below. Alternatively, the reference elements 124 may be located outside of the patient's body, e.g., affixed to the patient's skin, in order to establish an external three-dimensional coordinate system.

In any event, the controller/processor 126 can establish a three-dimensional coordinate system by controlling and processing signals transmitted between the spaced apart reference elements 124. In essence, the three-dimensional coordinate system provides an absolute framework in which all spatial measurements will be taken. The controller/processor 126 can also determine the positional coordinates of the location elements 122, and thus the distal end of the mapping/ablation catheter 108, within this coordinate system. As will be described in further detail below, this positional information can ultimately be used to graphically reconstruct a chamber of the heart 10, as well as the valves and vessel ostia of the heart 10. In the case illustrated in FIG. 2, the left atrium 12, the mitral valve 14, pulmonary vein 16, and ostium 18 of the pulmonary vein 16 are graphically reconstructed. The positional information will also ultimately be used to graphically reconstruct the distal end of the mapping/ablation catheter 108 (as well as any reference catheters 128), track the movement of the mapping/ablation catheter 108 within the heart chamber, heart valves, and vessel ostia, and, in conjunction with the mapping data obtained from the mapping processor 110, generate an electrophysiological map.

In the illustrated embodiment, the localization subsystem 104 employs ultrasound triangulation principles to determine the coordinates of the location elements 122 carried by the mapping/ablation catheter 108. In this case, the location and reference elements 122, 124 take the form of ultrasound transducers. The coordinates of the location elements 122 can be determined within an internal reference frame established by arranging the reference elements 124 in three-dimensional space. For example, the first two dimensions of the coordinate system can be provided by placing a reference catheter 128 within the coronary sinus (CS) (not shown) of the heart 10, thereby disposing its reference elements 124 in a two-dimensional plane. The third dimension can be provided by placing another reference catheter 128 within the right ventricular (RV) apex (not shown) of the heart 10 to dispose its reference elements 124 off of the two-dimensional plane. Notably, only four reference elements 124 are needed to provide the three dimensions. Any remaining reference elements 124 can be used to improve the accuracy of the triangulation process.

The controller/processor 126 is operated to sequentially transmit ultrasound pulses (e.g., 500 KHz pulses) through each reference element 124, and then measure the time delay between the respective transmit and receive pulses at the location element 122 and other reference elements 124. The controller/processor 126 then calculates the relative distances between each reference element 124 and the remaining reference elements 124 and location elements 122 using the "time of flight" and velocity of the ultrasound pulses. The distance information can be calculated as $d=vt$, where d is the distance between the transmitter and receiver, v is the velocity of the ultrasound signal within the medium (i.e., blood), and t is the time delay. To simplify the distance computations, the velocity of the ultrasound pulses may be assumed to be constant. This assumption typically only produces a small error when the reference elements 124 are located inside the body, since the velocity of ultrasound propagation is approximately the same in body tissue and blood.

The controller/processor 126 then establishes a three-dimensional coordinate system by triangulating the distances between the reference elements 124, and determines the positions of each of the location elements 122 within that coordinate system by triangulating the distances between the reference elements 124 and the location elements 122. Additional details on determining the positions of ultrasound transducers within a three-dimensional coordinate system can be found in U.S. Pat. No. 6,490,474 and U.S. patent application Ser. No. 09/128,304, entitled "A dynamically alterable three-dimensional graphical model of a body region," which are fully and expressly incorporated herein by reference.

It should be noted that there are other means for determining the positions of catheters within a three-dimensional coordinate system. For example, magnetic tracking techniques, such as that disclosed in U.S. Pat. No. 5,391,199, which is expressly incorporated herein by reference, can be employed. As another example, a voltage tracking technique, such as that disclosed in U.S. Pat. No. 5,983,126, which is expressly incorporated herein by reference, can be employed.

III. Graphical User Interface

Figure 5:
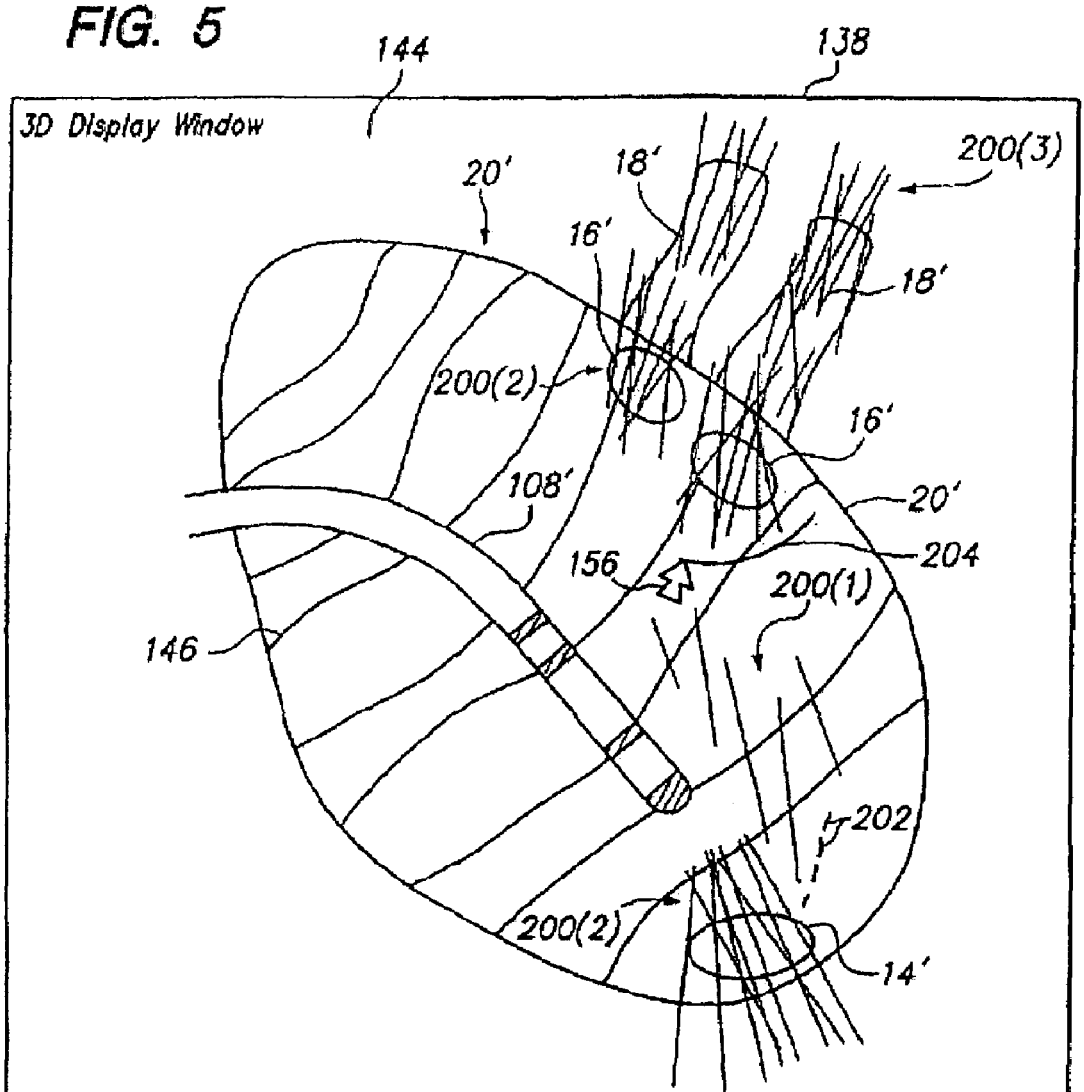
FIG. 5 is a front view of a monitor displaying graphical representations of the mapping/ablation catheter of FIG. 3, the endocardial surface of the left atrium of FIG. 2, and a superimposed electrical activity map.

Referring still to FIG. 1, the graphical user interface 106 comprises a graphical processor 134, a user input device 136, and an output device 138 (and specifically, a monitor). The graphical processor 134 is configured for generating a representation of the surface of an internal anatomical structure (in this case, the endocardial surface 20 within the left atrium 12 of the heart 10) in the form of a computer-generated graphical representation 20', which is then displayed in a 3-D display window 144 on the monitor 138, as illustrated in FIG. 5. The three-dimensional graphical processor 134 accomplishes this by acquiring the positions of the location elements 122 within the global coordinate system from the localization subsystem 104 as the mapping/ablation catheter 108 is moved around within the cavity of the internal anatomical structure, and then deforming the surface representation 20' (in particular, an anatomical shell) to the position of the distal tip of the catheter 108, which is extrapolated from the acquired positions of the location elements 122 and the known geometry of the catheter 108. As will be described in further detail below, the surface representation 20' can be initially deformed to include interior points (i.e., points periodically acquired, e.g., once every heart, while the distal end of the catheter 108 is moved around in the left atrium 12) and subsequently refined to include surface points (i.e., points taken at designated times when the distal catheter tip 120 is touching the endocardial surface 20 of the left atrium). Although only the endocardial surface 20 within the left atrium 12 is shown reconstructed in FIG. 5, it should be noted that the other chambers (right atrium and left and right ventricles) of the heart 10 can be graphically reconstructed in the same manner by moving the distal end of the catheter 108 within the respective chambers to acquire interior and surface points.

The graphical processor 134 is also configured for generating a representation of orifices (in this case, the mitral valve 14 and PV ostia 16) and vessels (in this case, a PV 18) associated with the heart 10 in the form of a computer-generated graphical representations 14', 16', and 18' within the established coordinate system, which is then displayed in a 3-D display window 144 on the monitor 138, as illustrated in FIG. 5. The three-dimensional graphical processor 134 accomplishes this by acquiring the positions of the location elements 122 within the coordinate system from the localization subsystem 104 as the distal end of the mapping/ablation catheter 108 is moved around within the orifices and vessels, and then generating straight line segments 200, each of which can be calculated by connecting the positions of the two distal most location elements 122 on the catheter 108. Because these two location elements 122 are located on the straight catheter section 115, each line segment 200 represents the distal end of the catheter 108 at a different location within the orifices and vessels. Notably, if the catheter 108, instead has a different preshaped section, such as a curved section, the line segments will be curvilinear that conform to the curved preshaped section. However, because the geometry of a straight catheter section can be more easily and accurately represented, and graphical representations of the orifices and vessels can be more easily and accurately generated based on straight line segments (as will be discussed in further detail below), the pre-shaped catheter section and associated line segments are preferably straight.

As shown in FIG. 5, some of the line segments 200(1) are completely inside of the surface representation 20' (formed when the straight catheter section 115 was completely located within the atrium 12), some of the line segments 200(2) are within the graphical mitral valve and PV ostium representations 14', 16' (formed when the straight catheter section 115 was inserted within the mitral valve 14 and PV ostia 16), and some of the line segments 200(3) are within the graphical PV representations 18' (formed when the straight catheter section 115 was completely inserted within the pulmonary veins 18). As will be described in further detail below, the graphical processor 134 conforms the graphical mitral valve and PV ostia representations 16', 18' to the line segments 200(2). In this manner, the need to graphically generate accurate representations of orifices by carefully and tediously touching the mitral valve 14 and the PV ostia 16 with the catheter distal tip 120 is obviated. As will also be described in further detail below, the graphical processor 134 conforms the graphical PV representations 18' to the line segments 200(3). Notably, because the line segments 200 provide more information than individual points, the number of measurements needed to be taken within the PV's 18 by the catheter 108 is reduced.

In addition to generating graphical representations of anatomical structures, the graphical processor 134 is also configured for generating a graphical representation 108' of the mapping/ablation catheter 108 within the established coordinate system, which is then superimposed over the graphical heart representation 10' in the 3D display window 144, as illustrated in FIG. 5. The graphical processor 134 can generate the graphical catheter model 108' from a pre-stored graphical model of the catheter 108, which can be deformed in accordance with the calculated positional coordinates of the location elements 122 carried by the catheter 108. In the illustrated embodiment, the graphical catheter representation 108' is dynamically generated in real-time. That is, the catheter representation 108' is graphically generated in successive time periods (e.g., once every heartbeat), so that it moves and bends as the actual catheter 108 is moved and bent within the heart chamber. The graphical processor 134 may optionally be configured to generate graphical representations of the reference catheters 128 (not shown) in real-time.

The graphical processor 134 is also configured for generating an electrical activity map 146 within the established coordinate system, which is then superimposed over the graphical heart representation 10' in the 3D display window 144, as illustrated in FIG. 5. The graphical processor 134 can generate the electrical activity map 146 based on the electrical activity information acquired from the mapping/ablation subsystem 102 and the positions of the mapping electrodes 116 geometrically derived from the positions of the location elements 122 obtained from the localization subsystem 104. This electrical activity map illustrates sites of interest, e.g., electrophysiology recording and ablation sites, for providing subsequent ablative treatment, and can be provided in the form of an isochronal or isopotential map. The electrical activity information may also be displayed separately from the 3D display window 144.

Additional details on graphically generating heart chambers, catheters, and electrical activity maps within a three-dimensional environment can be found in U.S. Pat. No. 6,490,474 and U.S. patent application Ser. No. 09/128,304, entitled "A dynamically alterable three-dimensional graphical model of a body region," which have previously been incorporated herein by reference.

The user input device 136 allows the user to interact with the graphics displayed on the monitor 138, and comprises a standard keyboard 140 and a graphical pointing device 142, such as a mouse. The graphical processor 134 responds to the user input device 136 by manipulating the graphics within the 3D display window 144. As an example, the user may rotate the 3D display window 144 in three-dimensions and "zoom" towards or away from the window 155 by clicking on the appropriate icon in the manipulation box 148 using the mouse 142. The user may also select one of the standard orientations, used in fluoroscopy, such as anterior-posterior (AP), lateral, right anterior oblique (RAO) or left anterior oblique (LAO) by selecting the appropriate icon in orientation box 150 using the mouse 142. The user may also select which catheters to display in real-time by checking the appropriate icons in the real-time box 152 using the mouse 142.

Using the mouse 142, the user can also mark anatomical regions of interest on the heart model by placing a cursor 156 at the appropriate location on the surface representation 20' and clicking. In the illustrated embodiment, the user can either mark the endocardial surface representation 20' with point markings 202 or with line markings 204 (either linear or curvilinear). For example, if the user desires to place a point marking 202 at an anatomical region of interest, the appropriate icon in the marking box 154 can be clicked, and then the user can mark the surface representation 20' by moving the cursor 156 to a selected region on the surface representation 20' and clicking the mouse 142. The surface representation 20' can be marked with additional points markings 158 in the same manner. If the user desires to place a line marking 204 at an anatomical region of interest, the appropriate icon in the marking box 154 can be clicked, and then the user can mark the surface representation 20' by clicking the mouse 142, and dragging the cursor 156. If curvilinear, the line marking 204 may either be open or closed. The user may also erase marks 202/204 from the surface representation 20' by clicking on the appropriate icon in the marking box 154, and them moving the cursor 156 over the mark 202/204, while clicking the mouse 142.

The user may also select whether the graphical processor 134 performs "passive chamber deformation," which deforms the surface representation 20' outward to include outerlying interior points acquired by the catheter 108 over successive time periods (e.g., every heart beat) or "snap deformation," which deforms the anatomical shell to a surface point acquired by the catheter 108 (preferably, somewhere on the endocardial surface 20) when designated by the user. The user may click the "Passive Deformation" icon 156 using the mouse 142 to prompt the graphical processor 134 to perform passive chamber deformation as the distal end of the catheter 108 is moved within the left atrium 12 of the heart 10, or may click the "Snap Deformation" icon 158 using the mouse 142 to prompt the graphical processor 134 to perform snap deformation each time the distal catheter tip 120 is placed into contact with the endocardial surface 20 of the left atrium 12.

Using the mouse 142, the user can also cause the graphics processor 134 to graphically generate orifice and vessel representations, such as the previously described mitral valve, PV ostium, and PV representations 14, 16, 18. In particular, the user may click either the "Orifice Creation" icon 162 or the "Vessel Creation" icon 164 with the mouse 142, which prompts the graphical processor 134 to graphically generate line segments 120 as the straight catheter section 115 is moved during successive time periods (e.g., every heart beat). When the "Orifice Creation" icon 160 is clicked, the graphical processor 134 is also prompted to graphically generate a representation of an orifice (e.g., the mitral valve 14 or PV ostia 16) around the line segments 200 that intersect the surface representation 20'. When the "Vessel Creation" icon 162 is clicked, the graphical processor 134 is prompted to both graphically generate a representation of an orifice (e.g., the PV ostia 16) around the line segments 200 that intersect the surface representation 20' and graphically generate a representation of a vessel (e.g., the PVs 18) around the line segments 200 that intersect or completely fall outside of the surface representation 20'. The user may also erase erroneously placed line segments 200, or line segments 200 that the user otherwise does not want the graphical processor 134 to consider when graphically generating the orifice and/or vessel representations, by clicking on the "Erase Line Segment" icon 164, and then moving the cursor 156 over the respective line segment 200, while clicking the mouse 142.

Figure 6:
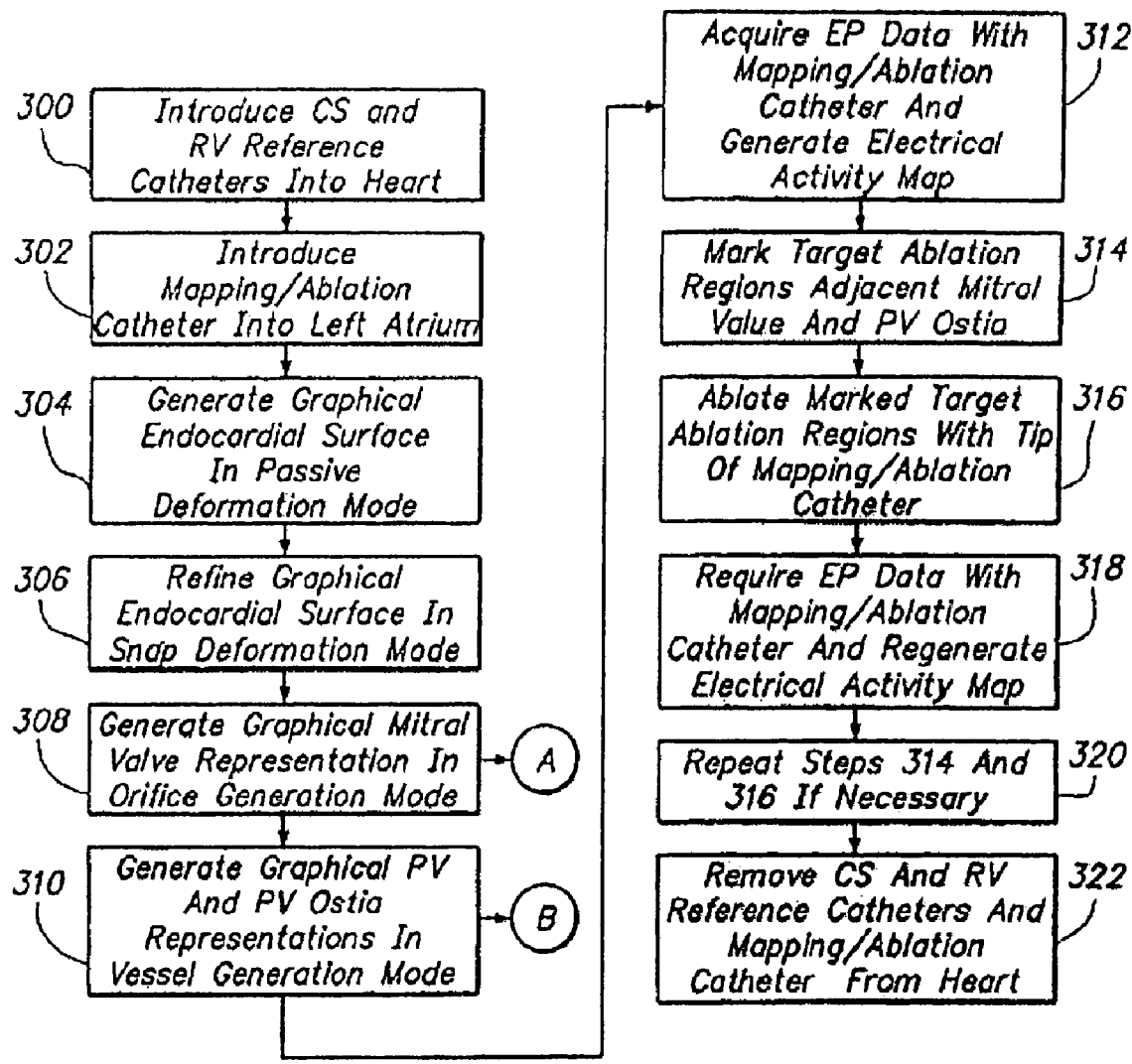
FIG. 6 is a flow diagram illustrating one method of diagnosing and treating atrial fibrillation using the medical system of FIG. 1.

Having described the structure of the medical system 100, one method of using the system 100 to locate and treat an aberrant conductive pathway within the heart 10, such as those typically associated with atrial fibrillation, will now be described with reference to FIG. 6. First, under fluoroscopy, the reference catheters 128 are intravenously introduced into the heart 10, and in particular, within the coronary sinus (CS) and right ventricle (RV) apex, so that the reference elements 124 are fixed within a three-dimensional arrangement (step 300). During introduction of the reference catheters 128, the localization subsystem 104 may be operated to transmit signals between the reference elements 124, so that the locations of the distal ends of the reference catheters 128 can be determined and graphically displayed in the 3D display window 144 on the monitor 138. Next, the mapping/ablation catheter 108 is introduced into the left atrium 12 of the heart 10 under fluoroscopy (step 302). Of course, the catheter 108 can be introduced into other chambers of the heart 10, such as the left ventricle, e.g., if the disease to be treated is ventricular tachycardia. During the introduction of the catheter 108, the localization subsystem 104 may be operated to transmit signals between the reference elements 124 and the location elements 122, so that the locations of the distal end of the catheter 108 can be determined and graphically displayed in the 3D display window 144.

The graphical processor 134 is then operated in the "Passive Deformation" mode, and the catheter 108 is moved around within the selected chamber of the heart 10 as the position of the distal catheter tip 120 is determined (step 304). As a result, the graphical processor 134 generates the surface representation 20', which begins as a generally spherical shape, and deforms it to include the interior anatomical points that are acquired by the catheter 108 outside of the endocardial surface representation 20'. The graphical processor 134 can then be operated in the "Snap Deformation" mode to refine the surface representation 20', in which case, the distal tip of the catheter 108 will be placed against selected regions of the endocardial surface 20, so that the graphical processor 134 can deform the surface representation 20' to the surface points acquired by the distal catheter tip 120 (step 306). During its deformation in both Passive Deformation and Snap Deformation modes, the surface representation 20' is displayed in the 3D display window 144 on the monitor 138.

Figure 7:
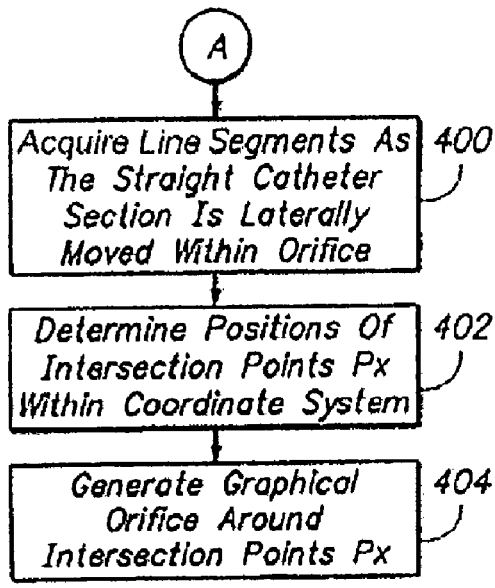
FIG. 7 is a flow diagram illustrating one method of graphically generating a representation of an orifice using the medical system of FIG. 1.
Figure 8:
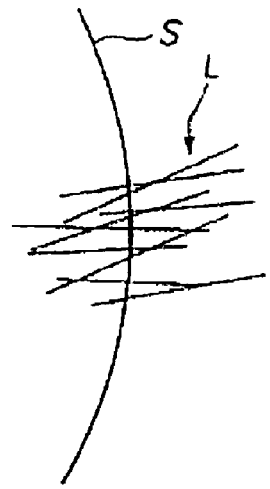
FIG. 8 is a side view showing the intersection of defined line segments with a graphical endocardial surface representation.

Next, the graphical processor 134 is operated in the "Orifice Generation" mode to generate representations of select orifices within the heart 10, and in this case, the mitral valve 14 (step 308). In particular, and with further reference to FIG. 7, the graphical processor 134 acquires line segments (shown referenced as L) representing the straight catheter section 115 as the straight catheter section 115 is laterally moved around in the orifice, and in this case, the mitral valve 14 (step 400). For each line segment L that intersects the surface representation (shown referenced as S) (see FIG. 8), the graphical processor 134 determines the position of the corresponding intersection point $P_x$ (shown in FIG. 9) within the established coordinate system (step 402).

Figure 9:
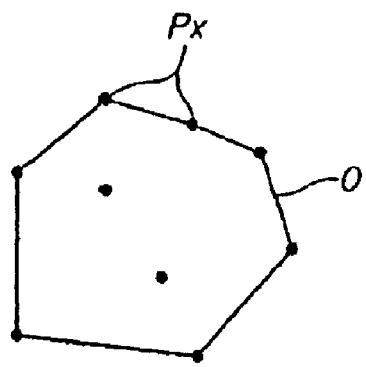
FIG. 9 is a cross-sectional view illustrating the graphical generation of a representation of an orifice around intersection points resulting from the intersection of the line segments of FIG. 8 with the surface representation.

The graphical processor 134 then generates the orifice representation O around the grouping of intersection points $P_x$ (step 404). This can be accomplished in any one of a variety of manners, but in the illustrated embodiment, an elliptical fit is performed when there are only a few intersection points $P_x$ available (e.g., less than five). As more line segments L, and thus intersection points $P_x$, are acquired, the orifice representation O can be refined, e.g., by connecting the outermost intersection points $P_x$ with lines, as illustrated in FIG. 9. Thus, it can be appreciated that the more line segments L that are acquired, the more smooth and realistic the graphical orifice representation O will become. It should be noted that a line segment L intersects the surface representation S to the extent that it traverses the surface representation S and need not have to actually contact the surface representation S. Notably, the first line segment L created will be touching the surface representation S, but once the orifice O is graphically generated, the subsequent line segments L may traverse the surface representation S without actually touching it.

Figure 10:
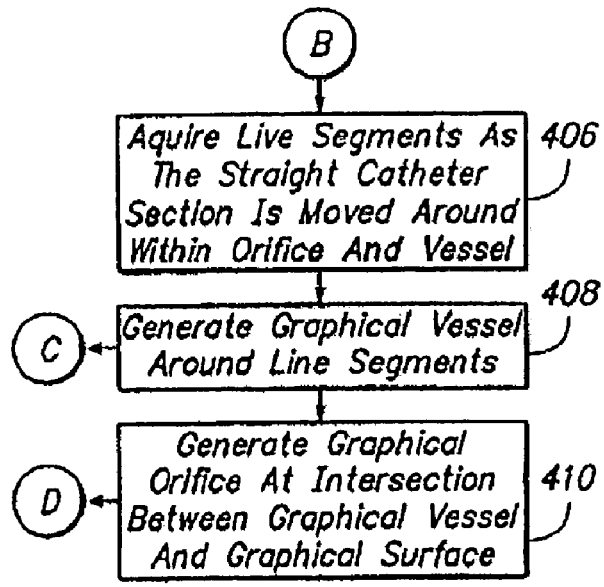
FIG. 10 is a flow diagram illustrating one method of graphically generating a representation of a vessel and associated ostium using the medical system of FIG. 1.
Figure 11:
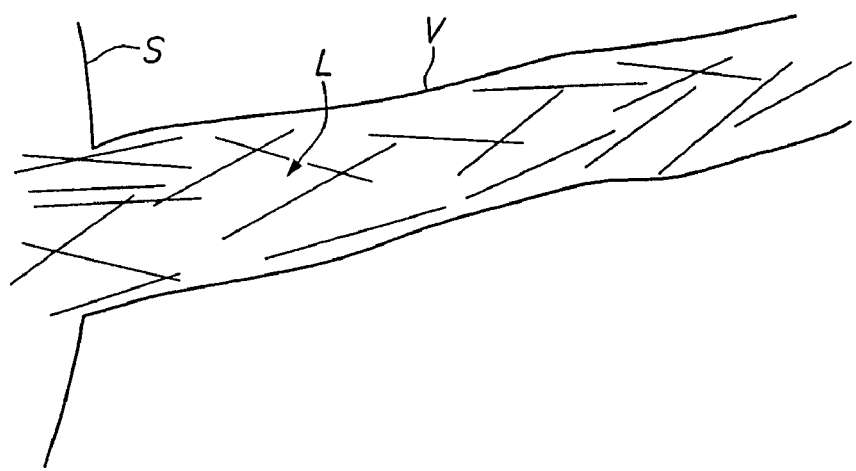
FIG. 11 is a side view showing the disposition of defined line segments within a graphical vessel representation.

Referring back to FIG. 6, the graphical processor 134 is operated in the "Vessel Generation" mode to generate representations of select vessels and associated ostia within the heart 10, and in this case, the PVs 18 and PV ostia 16 (step 310). In particular, and with further reference to FIG. 10, the graphical processor 134 acquires line segments L representing the straight catheter section 115 as the straight catheter section 115 is moved around in the selected orifice and vessel, and in this case, the PV ostia 16 and PVs 18 (step 406). The graphical processor 134 then generates a vessel representation V around the line segments L that at least partially extend outside of the surface representation S (i.e., those line segments L that both intersect and fall completely outside of the surface representation S) (step 408), as illustrated in FIG. 11. The graphical processor 134 then generates an orifice representation O at the location where the vessel representation V intersects the surface representation S (step 410).

Figure 13:
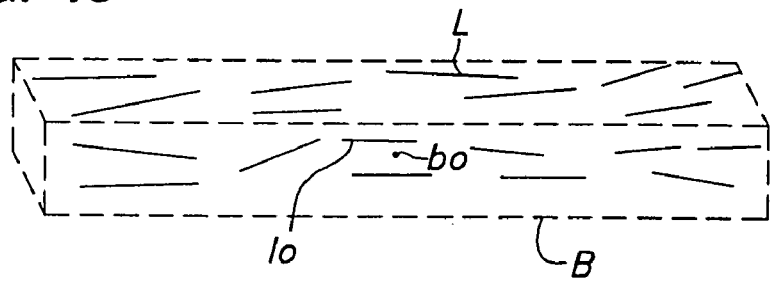
FIG. 13 is a perspective view of an initial bounding box defined around line segments disposed in a vessel.
Figure 14:
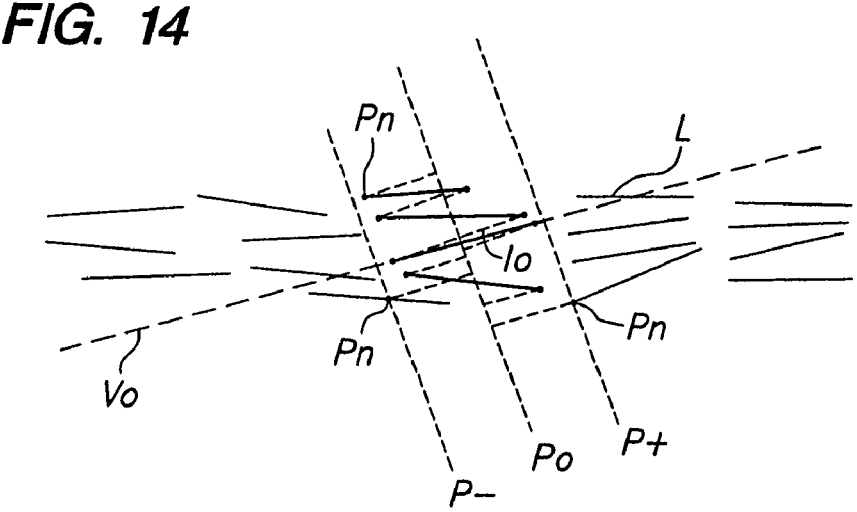
FIG. 14 is a schematic diagram illustrating the separation of parallel planes to select points to be projected onto a center plane.
Figure 12:
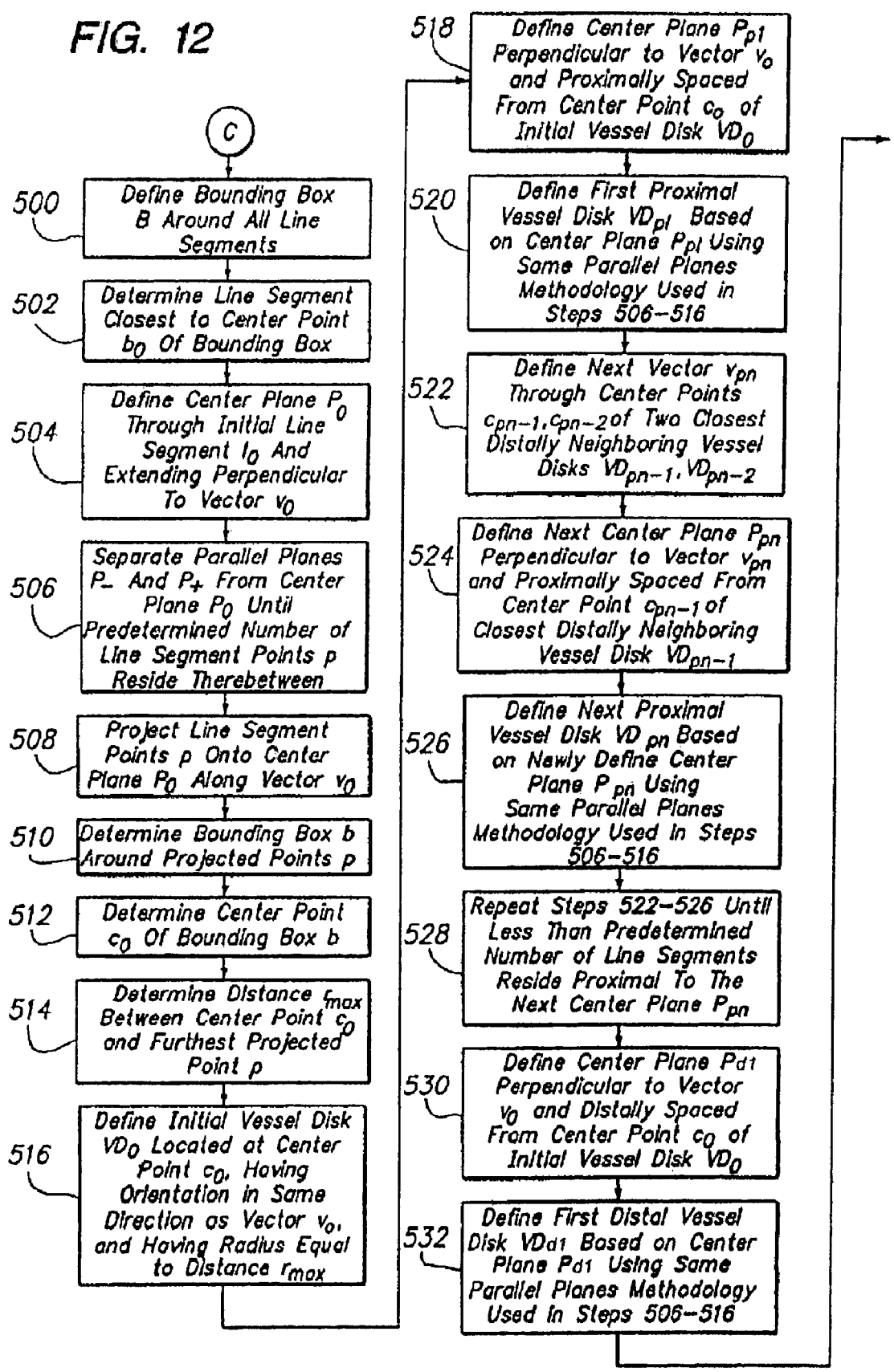
FIG. 12 is a flow diagram illustrating a detailed method of graphically generating a representation of a vessel using the medical system of FIG. 1.
Figure 12:
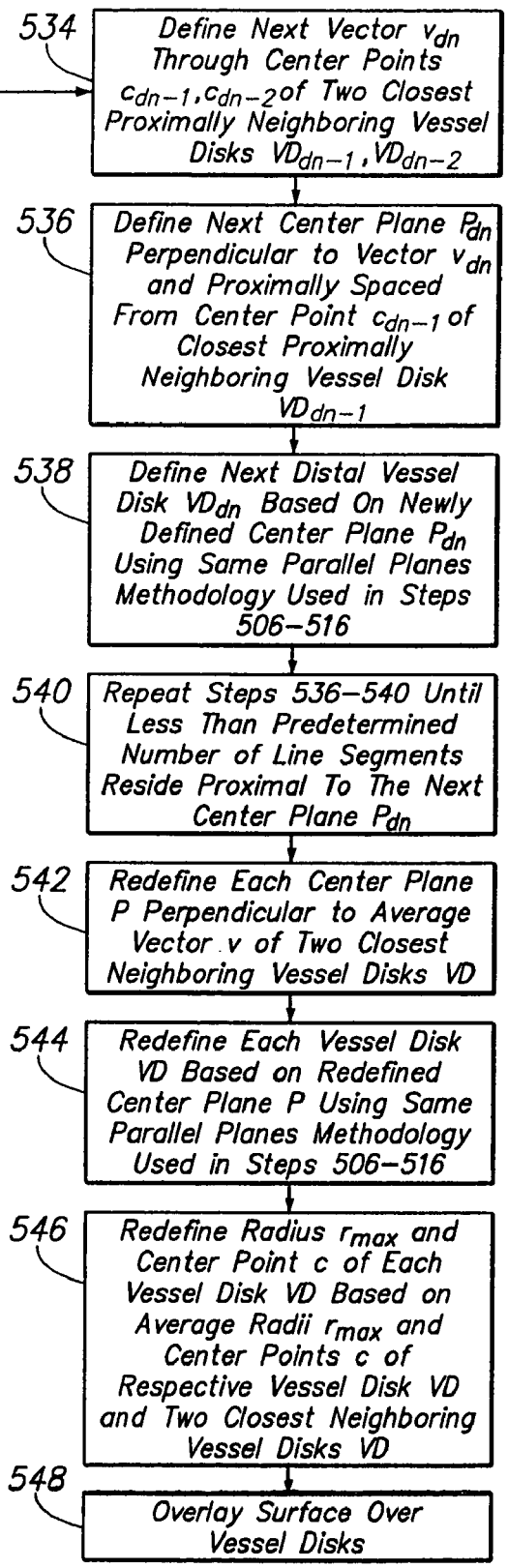

One detailed method of generating the vessel representation V by graphical generating a series of vessel construction disks VD (shown in FIG. 16) and overlaying those disks with a graphical vessel surface will now be described. Referring to FIG. 12, the graphical processor 134 first defines initial vessel disk $VD_0$ generally in the center of the line segment grouping (shown in FIG. 16). In particular, the graphical processor 134 defines a bounding box B around all of the line segments L (shown in FIG. 13) that at least partially extend outside of the surface representation S (step 500). The graphical processor 134 then determines an initial line segment $I_0$ that is closest to the center point $b_0$ of the bounding box b (step 502). As illustrated in FIG. 14, the graphical processor 134 then defines a center plane $P_0$ that extends through the center point of the initial line segment $I_o$ and oriented perpendicularly to a unit vector $v_0$ defined by the initial line segment $I_o$ (step 504).

Figure 15:
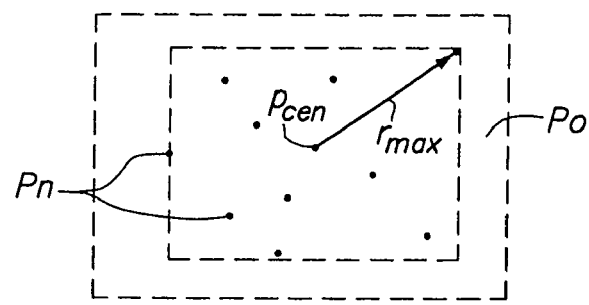
FIG. 15 is a schematic diagram illustrating the use of the projected points of FIG. 14 to define an initial vessel disk.
Figure 16:
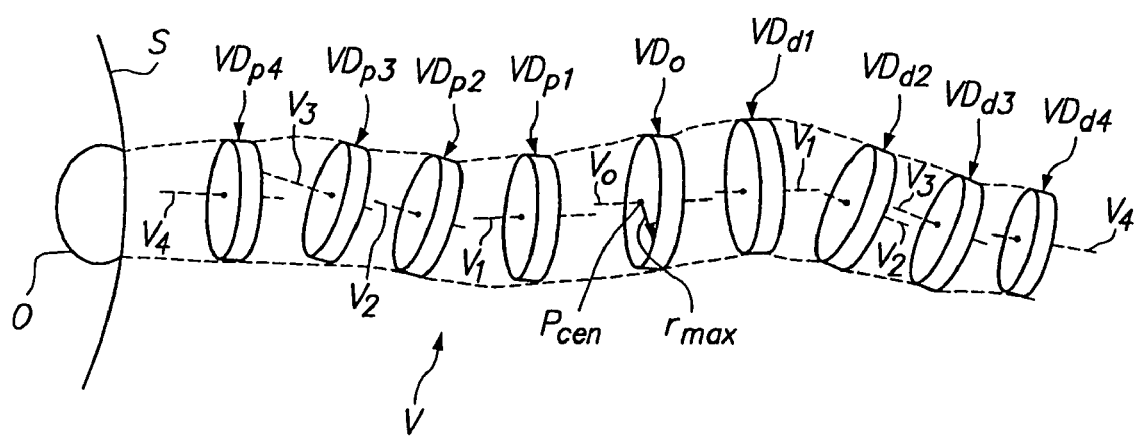
FIG. 16 is a perspective view illustrating a series of vessel disks used to generate the graphical vessel representation.

The graphical processor 134 then equidistantly separates parallel planes $P_-$ and $P_+$ from the center plane $P_0$ in opposite directions until a predetermined number of points p on the line segments (defined by the end points of the line segments L and any intersection points between the line segments and the parallel planes $P_-$ and $P_+$) reside between the parallel planes $P_-$ and $P_+$ (step 506). The predetermined number of points p required to reside within the parallel planes $P_-$ and $P_+$ will depend on the total number of line segments L from which the vessel representation V can be generated (i.e., the number of line segments L that intersect or are completely outside the surface representation S). In the illustrated method, if the total number of line segments L is less than 12, than the parallel planes $P_-$ and $P_+$ will be moved until two points p reside therein. If the total number of line segments L is less 12 or greater, than the parallel planes $P_-$ and $P_+$ will be moved until ten points p reside therein. After the parallel planes $P_-$ and $P_+$ have been separated the required distance, the graphical processor 134 projects the line segment points p onto the center plane P along the initial unit vector $v_0$, as illustrated in FIG. 15 (step 508). The graphical processor 134 then defines a bounding box b around the projected points p (step 510), determines the center point $c_0$ of the bounding box b (step 512), and then determines the distance $r_{max}$ between the center point $c_0$ and the farthest projected point p (step 514). As illustrated in FIG. 16, the graphical processor 134 then defines the initial vessel disk $VD_o$ within the three-dimensional coordinate system, which is located at the center point $c_0$ of the bounding box b, has an orientation in the same direction as the unit vector $v_0$, and has a radius equal to the distance $r_{max}$ (step 516).

After the initial vessel disk $VD_0$ has been defined, the graphical processor 134 defines subsequent vessel disks VD, and in particular, proximal vessel disks $VD_p$ that extend proximally from the initial vessel disk $VD_0$, and distal vessel disks $VD_d$ that extend distally from the initial vessel disk $VD_0$, as illustrated in FIG. 16.

Figure 17:
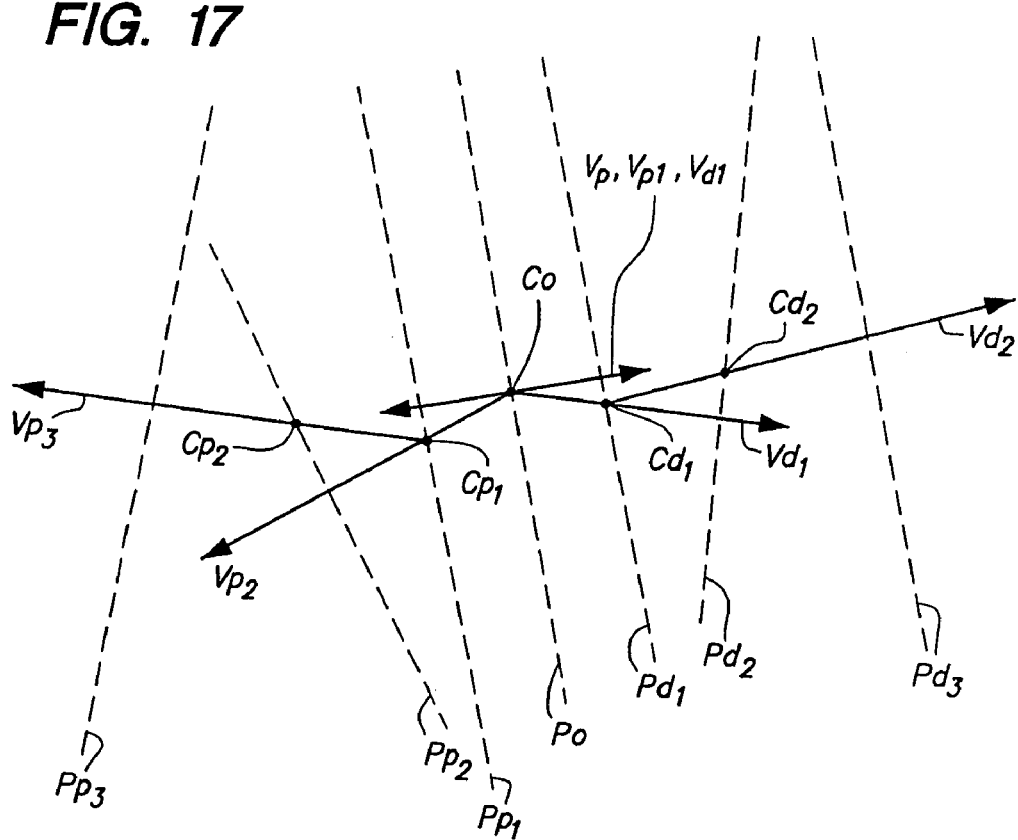
FIG. 17 is a schematic diagram illustrating the use of vectors associated with previous vessel disks to orient subsequent vessel disks.

In defining the subsequent proximal vessel disks $VD_p$, the graphical processor 134 initially defines the first proximal vessel disk $VD_{p1}$ (i.e., the proximal vessel disk immediately neighboring the initial vessel disk $VD_0$). In particular, the graphical processor 134 first defines a center plane $P_{p1}$ oriented perpendicularly to the unit vector $v_0$ of the initial vessel disk $VD_0$ and proximally spaced from the center point $c_0$ of the initial vessel disk $VD_0$ along the unit vector $v_0$ a predetermined distance (e.g., 5 mm) (step 518), as illustrated in FIG. 17. As can be seen, the new center plane $P_{p1}$ may intersect some of the same line segments L intersected by the previous center plane $P_0$—albeit at more proximal points along the line segments L. The graphical processor 134 then defines the first proximal vessel disk $VD_{p1}$ within the three-dimensional coordinate system based on the newly defined center plane $P_{p1}$ using the same parallel plane methodology previously used to define the initial vessel disk $VD_0$ (step 520).

The graphical processor 134 then defines the remaining proximal vessel segments L to conform to respective proximal sections of the line segment grouping. In particular, the graphical processor 134 first defines a unit vector $v_{pn}$ through the center points $c_{pn-1}$, $c_{pn-2}$ of the two closest distally neighboring vessel disks $VD_{pn-1}$, $VD_{pn-2}$ (shown in FIG. 17) (step 522). Notably, if the proximal vessel disk $VD_p$ currently defined is the second proximal vessel disk $VD_{p2}$, then the two closest distally neighboring vessel disks VD will be the first proximal vessel disk $VD_{p1}$ and the initial vessel disk $VD_0$, whereas if the proximal vessel disk $VD_p$ currently defined is the third or greater proximal vessel disk $VD_p$, the two closest distally neighboring vessel disks VD will both be proximal vessel disks $VD_p$.

The graphical processor 134 then defines a center plane $P_{pn}$ oriented perpendicularly to the unit vector $v_n$ and proximally spaced from the center point $c_{pn-1}$ of the closest neighboring proximal vessel disk $VD_{pn-1}$ along the unit vector $v_{pn}$ a predetermined distance (e.g., 5 mm), as illustrated in FIG. 17 (step 524). The graphical processor 134 then defines the next proximal vessel disk $VD_{pn}$ within the three-dimensional coordinate system based on the new center plane $P_{pn}$ using the same parallel plane methodology previously used to define the initial vessel disk $VD_0$ (step 526). Steps 522-526 are repeated until less than a predetermined number of line segments L (e.g., less than five) reside proximal to the next defined center plane $P_{pn}$ (step 528).

In defining the subsequent distal vessel disks $VD_d$, the graphical processor 134 initially defines the first distal vessel disk $VD_{d1}$ (i.e., the distal vessel disk VD immediately neighboring the initial vessel disk $VD_0$). In particular, the graphical processor 134 first defines a center plane $P_{d1}$ oriented perpendicularly to the unit vector $v_0$ of the initial vessel disk $VD_0$ and distally spaced from the center point $c_0$ of the initial vessel disk $VD_0$ along the unit vector $v_0$ a predetermined distance (e.g., 5 mm), as illustrated in FIG. 17 (step 530). As can be seen, the new center plane $P_{d1}$ may intersect some of the same line segments L intersected by the previous center plane $P_0$—albeit at more distal points along the line segments L. The graphical processor 134 then defines the first distal vessel disk $VD_{d1}$ within the three-dimensional coordinate system based on the newly defined center plane $P_{d1}$ using the same parallel plane methodology previously used to define the initial vessel disk $VD_0$ (step 532).

The graphical processor 134 then defines the remaining distal vessel segments L to conform to respective distal sections of the line segment grouping. In particular, the graphical processor 134 first defines a unit vector $v_n$ through the center points $C_{dn-1}$, $C_{dn-2}$ of the two closest proximally neighboring vessel disks $VD_{dn-1}$, $VD_{dn-2}$ (shown in FIG. 17) (step 534). Notably, if the distal vessel disk $VD_d$ currently defined is the second distal vessel disk $VD_{d2}$, then the two closest proximally neighboring vessel disks VD will be the first distal vessel disk $VD_d$, and the initial vessel disk $VD_0$, whereas if the distal vessel disk $VD_d$ currently defined is the third or greater distal vessel disk $VD_d$, the two closest distally neighboring vessel disks VD will both be distal vessel disks $VD_d$.

The graphical processor 134 then defines a center plane $P_{dn}$ oriented perpendicularly to the unit vector $v_{dn}$ and distally spaced from the center point $c_{dn-1}$ of the closest neighboring distal vessel disk $VD_d$ along the unit vector $v_{dn}$ a predetermined distance (e.g., 5 mm), as illustrated in FIG. 17 (step 536). The graphical processor 134 then defines the next distal vessel disk $VD_{dn}$ within the three-dimensional coordinate system based on the new center plane $P_{dn}$ using the same parallel plane methodology previously used to define the initial vessel disk $VD_0$ (step 538). Steps 534-538 are repeated until less than a predetermined number of line segments L (e.g., less than five) reside distal to the next defined center plane P (step 542).

It should be noted that although the method illustrated in FIG. 12 is described as defining all of the proximal vessel disks $VD_p$ prior to defining the distal vessel disks $VD_d$, all of the distal vessel disks $VD_d$ can be defined prior to defining the proximal vessel disks $VD_p$, or respective proximal and distal vessel disks VD can be alternately defined. The significance is that the proximal vessel disks $VD_p$ should be sequentially defined in a proximal direction from the initial vessel disk $VD_0$, and the distal vessel disks $VD_d$ should be sequentially defined in a distal direction from the initial vessel disk $VD_0$.

After all of the vessel disks VD have been initially defined, the center plane P associated with each of the vessel disks VD is redefined by calculating the average unit vectors $v_n$ associated with the two closest neighboring vessel disks VD (i.e., the closest proximally neighboring vessel disk VD and the closest distally neighboring vessel disk VD), and then reorienting the respective center plane P perpendicular to the averaged vector $v_n$ (step 542). The graphical processor 134 then redefines each vessel disk VD within the three-dimensional coordinate system based on each respective reoriented center plane P using the same parallel plane methodology previously used to define the initial vessel disk $VD_0$ (step 544).

Next, the graphical processor 134 smoothes the vessel disks VD by applying continuity requirements on the center points c and radii $r_{max}$. In particular, the center point c and radius $r_{max}$ of each vessel disk VD is redefined by taking the average of the center points c and radii $r_{max}$ of the respective vessel disk VD, the closest proximally neighboring vessel disk VD, and the closest distally neighboring vessel disk VD (step 546). Lastly, a graphical vessel surface V (shown in phantom in FIG. 16) is applied over the vessel disks VD from the endocardial surface representation S to the distal-most vessel disk VD (step 548).

graphically regenerating a representation of the surface;

It should be noted that although the graphical orifice and vessel generation processes have been described as being performed subsequent to the final graphical generation of the endocardial surface, in the preferred method, the endocardial surface generation need not be finalized prior to embarking on the graphical orifice and vessel generation process. For example, the graphical orifice and vessel generation process can be accomplished each time the endocardial surface representation is modified (with or without the definition of additional line segments). In the case of graphical orifice generation (whether in the "Orifice Generation" mode or the "Vessel Generation" mode), after the endocardial surface representation has been modified or otherwise refined, the already existing line segments will intersect the endocardial surface at different points. Thus, new intersection points within the coordinate system will then be defined, each of which representes an intersection of one of the line segments and the regenerated graphical surface representation. The representation of the orifice can then be regenerated based on the new intersection points.

Figure 18:
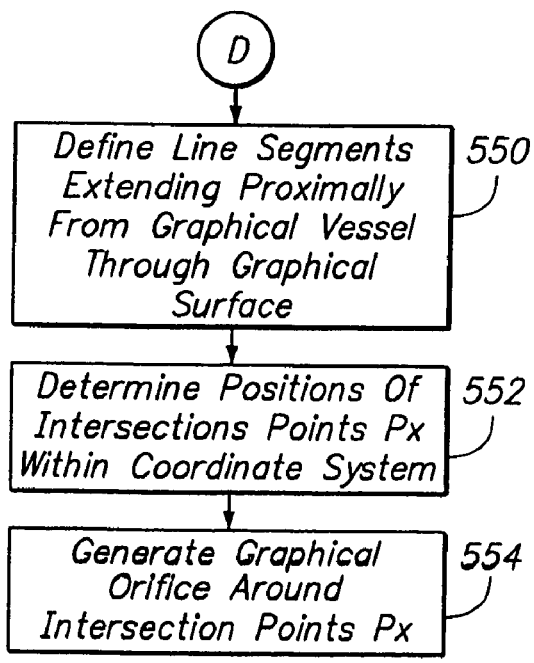
FIG. 18 is a flow diagram illustrating a detailed method of graphically generating a representation of an ostium of a vessel using the medical system of FIG. 1.

Referring back to FIG. 10, once the graphical vessel representation V has been generated, the graphical processor 134 generates a graphical representation of an orifice O (shown in FIG. 16) at the intersection between the vessel representation V and the endocardial surface representation S. In particular, and with further reference to FIG. 18, the graphical processor 134 defines line segments (not shown) that extend proximally from the periphery of the graphical vessel representation V through the graphical surface representation S (step 550). Alternatively, rather than generating line segments based on the graphical vessel representation V, the graphical processor 134 can acquire line segments as the straight catheter section 115 is moved around in the orifice in the same manner described in step 400 of FIG. 7. In either event, the graphical processor 134 then determines the positions of the intersection points $P_x$ created by the intersection of these line segments with the surface representation S (step 552), and then generates the orifice representation O around the grouping of intersection points $P_x$ (step 554). Steps 552 and 554 can be accomplished in the same manner as steps 402 and 404 are performed with reference to FIGS. 7, 8, and 9.

Referring back to FIG. 6, once the graphical endocardial surface, mitral valve, PV ostia, and PV representations 20', 14', 16', and 18' are generated (shown in FIG. 5), the mapping processor 110 is then operated to record electrical activity within the left atrium 12 of the heart 10 with the mapping/ablation catheter 108 and derive mapping data therefrom. The graphical processor 134 acquires this mapping data and generates the electrical activity map 146, which is then displayed on the 3D display window 144 (shown in FIG. 5) over the endocardial surface representation 20' (step 312).

If an aberrant region is identified, the user will then use the mouse 142 to graphically generate markings 202, 204 on the target ablation regions of the endocardial surface 20 (shown in FIG. 5), e.g., around the PV ostia 16 and extending down to the mitral valve 14 (step 314). Notably, the display of the mitral valve, PV ostia, and PV representations 14', 16', 18' provide a useful reference when generating the markings 202, 204. The distal tip 120 of the mapping/ablation catheter 108 is then placed into contact with the targeted tissue marks, and the RF generator operated 112 to therapeutically create a lesion on the mark (step 316). If the targeted tissue mark is a point marking 202 or a series of point markings 202, the lesion will take the form of a spot lesion or lesions. If the targeted tissue mark is a line marking 204, the lesion will take the form of a linear or curvilinear lesion. After the ablation process is complete, the mapping processor 110 can again be operated to ensure that the heart disease has been successfully treated by reacquiring the mapping data and regenerating the electrical activity map 146 for display on the 3D display window 144 over the endocardial surface representation 20' (step 318). If additional aberrant conductive pathways have been found, the marking and ablation steps can be repeated (step 320). If no aberrant conductive pathways have been found, the reference catheters 128 and mapping/ablation catheter 108 can then be removed from the heart 10 (step 322).

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A method of graphically creating a representation of an anatomical body having a surface with an orifice, comprising:
    graphically generating a representation of the surface within a coordinate system;
    laterally moving the distal end of an elongated probe within the orifice;
    defining line segments within the coordinate system while the probe distal end is moved within the orifice, each of the line segments representing the probe distal end;
    defining intersection points within the coordinate system using one or more processors, where each of the points representing an intersection of one of the line segments and the surface representation; and
    graphically generating a representation of the orifice based on the intersection points.

2. The method of claim 1, wherein the anatomical body is a heart chamber.

3. The method of claim 1, wherein the orifice is an ostium of a blood vessel.

4. The method of claim 3, wherein the blood vessel is a pulmonary vein.

5. The method of claim 1, wherein the orifice is valve.

6. The method of claim 5, wherein the valve is a mitral valve.

7. The method of claim 1, wherein the coordinate system is a three-dimensional coordinate system.

8. The method of claim 1, further comprising:
    graphically regenerating a representation of the surface;
    redefining new intersection points within the coordinate system, each of the new points representing an intersection of one of the line segments and the regenerated graphical surface representation; and
    graphically regenerating a representation of the orifice based on the new intersection points.

9. The method of claim 1, wherein the line segments are rectilinear.

10. The method of claim 1, wherein the step of defining each line segment comprises determining at least two points along the probe distal end within the coordinate system.

11. The method of claim 1, wherein the step of graphically generating the orifice representation comprises connecting outermost intersection points with lines to form a polygon.

12. The method of claim 1, wherein the step of graphically generating the orifice representation comprises fitting an ellipse around the intersection points.

13. The method of claim 1, wherein the anatomical body has a vessel and the orifice is an ostium of the vessel, the method further comprising graphically generating a representation of the vessel based on the line segments.

14. The method of claim 13, wherein the step of graphically generating the vessel representation comprises forming the graphical vessel representation around the line segments.

15. The method of claim 1, further comprising displaying the surface and orifice representations.

16. A medical system for use with an anatomical body having a surface with an orifice, comprising:
    an elongated medical probe having a distal section with a known geometry;
    one or more processors configured for:
    graphically generating a representation of the surface within a three-dimensional coordinate system;
    defining line segments within the coordinate system, each of which represents the probe distal end;
    defining intersection points within the coordinate system, each of which represents an intersection of one of the line segments and the surface representation; and
    graphically generating a representation of the orifice based on the intersection points.

17. The system of claim 16, wherein the coordinate system is a three-dimensional coordinate system.

18. The system of claim 16, wherein the one or more processors are configured for:
    graphically regenerating a representation of the surface;
    redefining new intersection points within the coordinate system, each of the new points representing an intersection of one of the line segments and the regenerated graphical surface representation; and
    graphically regenerating a representation of the orifice based on the new intersection points.

19. The system of claim 16, wherein the probe comprises an intravascular catheter.

20. The system of claim 16, wherein the wherein the distal probe section has a rectilinear geometry, and the line segments are rectilinear.

21. The system of claim 16, wherein the one or more processors are configured for defining each line segment by determining at least two points along the probe distal end within the coordinate system.

22. The system of claim 16, wherein the one or more processors are configured for graphically generating the orifice representation comprises by connecting outermost intersection points with lines to form a polygon.

23. The system of claim 16, wherein the one or more processors are configured for graphically generating the orifice representation by fitting an ellipse around the intersection points.

24. The system of claim 16, wherein the anatomical body has a vessel and the orifice is an ostium of the vessel, and wherein the one or more processors are configured for graphically generating a representation of the vessel based on the line segments.

25. The system of claim 24, wherein the one or more processors are configured for graphically generating the vessel representation by forming the graphical vessel representation around the line segments.

26. The system of claim 16, further comprising an output device configured for displaying the surface and orifice representations.

* * * * *

UNITED STATES PATENT AND TRADEMARK OFFICE
CERTIFICATE OF CORRECTION

| | | |
|---|---|---|
| PATENT NO. | : 7,633,502 B2 | Page 1 of 1 |
| APPLICATION NO. | : 10/850357 | |
| DATED | : December 15, 2009 | |
| INVENTOR(S) | : Willis et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1610 days.

Signed and Sealed this

Ninth Day of November, 2010

David J. Kappos
*Director of the United States Patent and Trademark Office*